United States Patent [19]

Brems et al.

[11] Patent Number: 5,559,094
[45] Date of Patent: Sep. 24, 1996

[54] ASP$^{B1}$ INSULIN ANALOGS

[75] Inventors: David N. Brems; Diane L. Bakaysa, both of Indianapolis, Ind.

[73] Assignee: Eli Lilly and Company, Indianapolis, Ind.

[21] Appl. No.: 285,661

[22] Filed: Aug. 2, 1994

[51] Int. Cl.$^6$ .................. C07K 14/62; A61K 38/28; C12N 15/00; C12N 15/17
[52] U.S. Cl. .................. 514/3; 514/4; 530/303; 530/304; 530/305; 530/866
[58] Field of Search ..................... 530/303, 304, 530/305, 866; 514/3, 4; 435/69.4

[56] References Cited

U.S. PATENT DOCUMENTS

4,617,149  10/1986  DiMarchi et al. ............... 530/324

FOREIGN PATENT DOCUMENTS

383472  8/1990  European Pat. Off. .

OTHER PUBLICATIONS

Brader, et. al., "Insulin hexamers: new conformations and applications", *Trends In Biochemical Sciences,* 16:341–345 (1991).
Derewenda, et al., "Phenol stabilizes more helix in a new symmetrical zinc insulin hexamer", *Nature,* 338:594–596 (1989).
Chothia, et al., "Transmission of conformational change in insulin", *Nature,* 302: 500–505 (1983).
Kruger, et. al., "Cooperativity and Intermediate States in the T→R Structural Transformation of Insulin", *Biol. Chem. Hoppe–Seyler,* 371: 669–673 (1990).
Bentley, et. al., "Structure of insulin in 4–zinc insulin", *Nature,* 261: 166–168 (1976).
Smith et. al., "The Structure of a Rhombohedral R$_6$ Insulin Hexamer That Binds Phenol", *Biopolymers,* 32: 441–445 (1992).
Renscheidt, et. al., "A Solution Equivalent of the 2Zn→4Zn transformation of insulin in the crystal", *Eur. J. Biochem,* 142: 7–14 (1984).
Brader, et. al., "Characterization of the R–State Insulin Hexamer and Its Derivatives. The Hexamer Is Stabilized by Heterotropic Ligand Binding Interactions", *Biochemistry,* 30: 6636–6645 (1991).
Brange, et. al., "Chemical Stability of Insulin 2. Formation of Higher Molecular Weight Transformation Products During Storage of Pharmaceutical Preparations", *Pharmaceutical Research* 9: No. 6, 727–734 (1992).
Brange, et. al., "Chemical stability of insulin 3. Influence of excipients, formulations, and pH" *Acta Pharm. Nord.,* 4: 149–158 (1992).
Brange, et. al., "Chemical Stability of Insulin. 1. Hydrolytic Degradation During Storage of Pharmaceutical Preparations", *Pharmaceutical Research,* 9: No. 6, 715–726 (1992).
Brems, et, al. "Improved insulin stability through amino acid substitution" *Protein Engineering,* 5 (No. 6), 519–525 (1992).
Brange, et, al., "Monomeric Insulins and Their Experimental and Clinical Implications", *Diabetes Care,* 13, No. 9, 923–954 (1990).

Brange, et. al., "Designing insulin for diabeses therapy by protein engineering" *Current Opinion in Structural Biology,* 1, 934–940 (1991).
DiMarchi, et. al., "Synthesis of a fast–acting insulin based on structural homology with insulin–like growth factor I", *Peptides: Chemistry and Biology, Proceedings of the Twelfth American Peptide Symposium,* 26–28 (1992).
Goldman, et, al., "Zinc Binding, Circular Dichroism, and Equilibrium Sedimentation Studies on Insulin (Bovine) and Several of Its Derivatives" *Biochemistry,* 13, No. 22, 4566–4574 (1974).
Bentley, et. al., "Role of B13 Glu in Insulin Assembly" *J. Mol. Biol.* 228, 1163–1176 (1992).
Wollmer, et. al., "Structural Transition in the Metal–Free Hexamer of Protein–Engineered [B13 Gln] Insulin" *Biol. Chem. Hoppe–Seyler,* 370 1045–1053 (1989).
Wollmer, et. al., "Phenol–Promoted Structural Transformation of Insulin in Solution" *Biol. Chem. Hoppe–Seyler,* 368, 903–911 (1987).
Grant, et. al., "Differences in the Nature of the Interaction of Insulin and Proinsulin with Zinc" *Biochem. J.,* 126, 433–440 (1972).
Hol, et. al., "The a–helix dipole and the properties of proteins" *Nature,* 273, 443–446 (1978).
Shoemaker, et. al., "Tests of the helix dipole model for stabilization of a–helices" *Nature,* 326 563–567 (1987).
Presta, et. al., "Helix Signals in Proteins" *Science,* 240, 1632–1641 (1988).
Richardson, et. al., "Amino Acid Preferences for Specific Locations at the Ends of a Helices", *Science,* 240, 1648–1652 (1988).
Kline, et. al., "Complete Sequence–Specific $^1$H NMR Assignments for Human Insulin" *Biochemistry,* 29, 2906–2913 (1990).
Goeders, et. al., "Absorption Kinetics of Regular and Isophane (NPH) Insulin In The Normal Dog" *Domestic Animal Endocrinology,* 4(1): 43–50 (1987).
Blundell, et al. "Insulin: The Structure In The Crystal And Its Reflection In Chemistry and Biology",, *Adv. Protein Chem.,* 26:279–329 (1972).
Baker, et al, "The Structure of 2Zn Pig Insulin Crystals At 1.5Å Resolution" *Philos. Trans. R. Soc. London, B.,* 319: 369–456 (1988).
Merck Index (11th Edition), 789–790 (1989).
Frank, et al, "The production of Human Proinsulin And Its Transformation To Human Insulin And C–Peptide" *Peptides: Synthesis–Structure–Function, Proc. Seventh Am. Pept. Symp.* Eds.D. Rich and E. Gross, 729–738 (1981).

(List continued on next page.)

*Primary Examiner*—Marianne P. Allen
*Attorney, Agent, or Firm*—Ronald S. Maciak; Douglas K. Norman

[57] ABSTRACT

Analogs of human insulin containing an aspartic acid at position 1 of the B chain (Asp$^{B1}$), and optionally, having a gln modification at position 13 (Gln$^{B13}$), display modified physico-chemical and pharmacokinetic properties which enable them to be long acting. These analogs are useful in the treatment of hyperglycemia because they are soluble and display an increased tendency to self-associate.

18 Claims, 4 Drawing Sheets

OTHER PUBLICATIONS

Frank, et al, "Insulin and Proinsulin Conformation in Solution" *Diabetes*, 21 supp.2: 486–491 (1972).

Serrano, et al, "Capping and α–helix stability" *Nature* 342:296–299 (1989).

Markowitz, J., et al, "Experimental Surgery of the Pancreas" *Experimental Surgery Including Surgical Physiology*, 236–252 (1964).

Kornberg, et al, "Glucose–6–Phosphate Dehydrogenase" *Methods In Enzymology* 1:323–327 (1955).

Bathelmai, et al "Enzymatische Bestimmungen der Glucose in Blut, Liquor und Harn" *Klin. Wochenschr.* 40:585 (1962).

Monod, et al. "On The Nature of Allosteric Transistions: A Plausible Model" *J. Mol. Biol.* 12: 88∝118 (1965).

Binder, et al "A Theoretical Model for the Absorption of Soluble Insulin" *Artifical Systems For Insulin Delivery* edited by P. Brunetti, et al., Raven Press, N.Y. 53–57 1983).

Stewart, et al *Solid Phase Peptide Synthesis* Freeman and Co., San Francisco, 1–103 (1969).

Chance, et al, "The Production of Human Insulin Using Recombinant DNA Technology And A New Chain Combination Procedure" *Peptides: Synthesis–Structure–Function Proceedings of the Seventh American Peptide Symposium* Edited by D. H. Rich and E. Gross, 721–728 (1981).

SEQUENCE LISTING ( 1 ) GENERAL INFORMATION:

( i i i ) NUMBER OF SEQUENCES: 2

( 2 ) INFORMATION FOR SEQ ID NO:1 :

( i ) SEQUENCE CHARACTERISTICS:
        ( A ) LENGTH:21 amino acids
        ( B ) TYPE:amino acid
        ( C ) STRANDEDNESS:
        ( D ) TOPOLOGY:linear ( x i ) SEQUENCE DESCRIPTION: SEQ ID NO:1:

Gly Ile Val Glu Gln Cys Cys Thr Ser Ile Cys Ser Leu Tyr Gln Leu Glu
1                             5                             10

Asn Tyr Cys Asn
                20

( 2 ) INFORMATION FOR SEQ ID NO:2 :

( i ) SEQUENCE CHARACTERISTICS:
        ( A ) LENGTH:30 amino acids
        ( B ) TYPE:amino acid
        ( C ) STRANDEDNESS:
        ( D ) TOPOLOGY:linear ( i i ) MOLECULE TYPE:polypeptide ( i x ) FEATURE:
        ( A ) NAME/KEY:Variable Site
        ( B ) LOCATION: 13
        ( C ) IDENTIFICATION METHOD:
        ( D ) OTHER INFORMATION:"This amino acid is either Gln or Glu."

( x i ) SEQUENCE DESCRIPTION: SEQ ID NO:2:

Asp Val Asn Gln His Leu Cys Gly Ser His Leu Val Xaa Ala Leu
1                 5                     10                      15

Tyr Leu Val Cys Gly Glu Arg Gly Phe Phe Thr Thr Pro Lys Thr
                    20                      25                      30

ASP$^{B1}$ INSULIN ANALOGS

FIELD OF THE INVENTION

The present invention relates to the field of human medicine, particularly the treatment of diabetes. Most specifically, the invention relates to Asp$^{B1}$ analogs of the human insulin molecule, methods of using these analogs and pharmaceutical compositions comprising these insulin analogs.

BACKGROUND OF THE INVENTION

Diabetes mellitus is a metabolic disorder characterized by the failure of body tissues to oxidize carbohydrates at the normal rate. A deficiency of insulin is the most important factor in the diabetic disease state. During the last 70 years people suffering from diabetes have been greatly aided by receiving controlled amounts of insulin. Until the early 1980's, the insulin used by diabetics was isolated from animal pancreases, generally bovine and porcine. With the introduction of recombinant DNA technology it has become possible to produce large amounts of natural human insulin as well as naturally and non-naturally occurring analogs of human insulin using known synthetic methods. The analogs can also be chemically synthesized. These insulin analogs display different physical and chemical properties when compared to natural human insulin. One such property is to decrease the rate of action of the insulin so that the dosage can be metered into the patient over time as a result of implanting a single dosage.

The human insulin monomer is composed of two chains, the 21 amino acid A chain and the 30 amino acid B chain, that are covalently attached by two interchain disulfide bonds (Merck Index (11th Edition, 789–790 (1989)). In the presence of Zn, natural human insulin associates to a hexamer with 2 Zn atoms coordinated octahedrally to H$^{B10}$ of each monomer and 3 water molecules (Blundell, et al., Adv. Protein Chem., 26, 279–402 (1972); and Baker, et al., Philos, Trans. R. Soc. London, B 319, 369–456 (1988)). The 2 Zn insulin hexamer functions as an allosteric protein. Phenolic ligands or certain salts are capable of inducing a conformational transition, resulting in the N-terminal 8 amino acids of the B chain converting from an extended conformation to an Q-helix. The two Zn atoms become tetrahedrally coordinated to H$^{B10}$ of each monomer and a fourth solvent-accessible site occupied by small anionic ligands, i.e., Cl ion (Brader & Dunn, TIBS, 16, 341–345 (1991)). This conformational state induced by phenolic ligands has been referred to as the R state and the apoinsulin form as the T state, named after the general nomenclature of Monod et al. (Monod, et al., J. Mol. Biol., 12 88–118 (1965)). The R state is more compact, less flexible, and the Zn exchange is retarded compared to the T state (Derewenda et al., Nature, 338, 594–596 (1989)). The insulin T–>R conversion involves the movement of >30Å of the B$^1$ α-carbon (Derewenda et al., Nature, 338, 594–596 (1989)), which is the largest distance transversed by any atom associated with an allosteric conformational transition. A stable intermediate state, T$_3$R$_3$ has been identified that has one trimer in the T state and the other in the R state (Chothia et al., Nature, 302, 500–505 (1983)). The T$_3$R$_3$ state was formally known as the 4-Zn insulin structure which is induced by salts or by limited amounts of phenolics (Kruger, et al., Biol. Chem. Hoppe-Seyler, 371, 669–673 (1990)).

The different allosteric states of insulin hexamer have been best characterized in the crystal state by X-ray crystallography (Bentley et al., Nature, 261, 166–168 (1976); Smith & Dodson, Biopolymers, 32, 441–445 (1992)), in solution by proton NMR, circular dichroism (Renscheidt et al., Eur. J. Biochem., 142, 7–14 (1984), and visible absorption spectroscopy of Co$^{2+}$ substituted insulins (Brader et al., Biochemistry, 30, 6636–6645 (1991)). The biological significance of insulin allosterism has not been fully elucidated. The biologically active form of insulin is thought to be a monomer due to the dilute concentrations of insulin in the blood circulation (Frank et al., Diabetes, 21 (Suppl. 2), 486–491 (1972)). A receptor-mediated conformational change in the insulin conformation is thought to be required for binding. A conformational change similar to the T–>R transition, which is induced by the receptor, has been proposed (Derewenda et al., Nature 338, 594–596 (1989)). For the medicinal use of insulin, the T–>R conformations have important consequences. Most formulations of insulin are solutions or suspensions that contain phenolics that function as preservatives against bacterial contamination. The phenolic concentrations in insulin formations are 2–10 times that necessary to induce the R conformation (Kruger et al., Biol. Chem. Hoppe-Seyler, 371, 669–673 (1990)). The presence of phenolics in insulin formations has important consequences on the shelf-life stability (Brange et al., Pharm. Res., 9, 715–726 (1992a); Brange et al., Pharm. Res. 9, 727–734 (1992b); Brange & Langkjaer, Acta Pharm. Nord., 4, 149–158 (1992)) and possibly the time action profile. The solution state storage of insulin has been explained by a thermodynamic model (Brems et al., Protein Engineering, 5, 519–525 (1992)), wherein insulin degradation is governed by the equilibrium constant of unfolding, Keq. The equilibrium constant determined from the reaction N<—>U is U/N, where N=native and U=unfolded. Since the R state of insulin is most compact, least flexible, and the exchange of Zn is retarded, the R state is expected to provide the greatest protection from degradation. Minimizing degradation of insulin formulations is extremely important in reducing undesirable side effects of insulin therapy.

Undoubtedly, millions of patients have benefitted by the serendipitous choice of the original formulators of insulin to use phenolic preservatives. The rate of absorption of insulin from the depot injection site has been shown to be related to the dissociation constant for self-association (Brange, et al., Diabetes Care, 13, 923–954 (1990)). Monomers are thought to be the state that is readily absorbed and the dissociation process to be rate limiting (Binder, C., Artificial Systems for Insulin Delivery, edited by P. Brunetti et al., Raven Press, N.Y., pages 53–57 (1983)). Insulin analogs that are monomeric have been shown to be rapidly absorbed and result in a rapid time action profile (Brange, et al., Curr. Opin. Struct. Biol., 1, 934–940 (1991); DiMarchi et al., Peptides: Chemistry and Biology, Proceedings of the Twelfth American Peptide Symposium, ESCOM, Leiden, pp. 26–28 (1992)). Conversely, insulin forms that have increased association constants should prolong the rate of absorption and the time action profile.

All current intermediate to slow acting insulin formulations are suspensions. When these insulin formulations are injected subcutaneously, they form a depot from which they are slowly absorbed into the blood stream. The dissolution of particles at the subcutaneous injection site is the rate-limiting process that causes delayed time action of these suspension formulations. Suspensions for parenteral use have inherent disadvantages compared to soluble formulations that include poor dosing accuracy, a requirement for resuspension before injection, and a propensity for clumping. A soluble slow-acting insulin formation would overcome these disadvantages and be highly desirable.

Soluble insulin formations demonstrate a lag in their absorption kinetics due to size constraints of the insulin hexamer whose uptake is delayed by dissociation to monomer which is readily absorbed (Brange, J., et al., Current Opinion in Structural Biology, 1, 934–940 (1991)). Various ligands are known to alter the self-association of insulin. As indicated, zinc causes soluble insulin to self-associate to the hexamer (Goldman, J., and Carpenter, F. H., Biochemistry, 13, 4566–4574 (1974)) and hexamers undergo the T–>R transition by the addition of the phenolics (Brader, M. L., et al., TIBS, 16, 341–345 (1991)). The presence of formulation excipients such as Zn and phenols are specific ligands for insulin hexamer and likely delay the dissociation to monomer at the injection site. The binding of phenol is considerably weaker than Zn, and thus the dissolution of insulin hexamer that occurs at the injection site is thought to proceed from the R-state to the T-state and ultimately to monomer.

One strategy for postponing insulin hexamer dislocation is to prevent dissociation using extrinsic ligands such as Zn and phenols. This could be accomplished by creating an insulin analog with the constitutive properties of these extrinsic ligands. The hexamer inducing properties of Zn can be obtained by substituting gluB13 for gluB13 (Bentley, G. A., et al., J. Mol. Biol. 228, 1163–1176 (1992)). The center of the insulin hexamer has six glutamic acids packed closely together causing an electrostatic repulsion and destabilization. By substituting these residues for neutral ones, the insulin analog forms stable hexamers even in the absence of Zn. However, the effect on insulin absorption rate after injection of a acidic solution of the $gln^{B13}$ analog is only reduced by 25% (Brange, J., et al., Current Opinion in Structural Biology, 1, 934–940 (1991)). Studies on a mutated insulin by Wollmer et al. (Wollmer et al., Biol. Chem. Hoppe-Seyler, 370, 1045–1053 (1989)) have shown a self-induced allosterism. $Glu^{B13}$ insulin plus Zn in the absence of other inducing allosteric ligands has CD spectral properties intermediate between the T and R states (Wollmer et al., Biol. Chem. Hoppe-Seyler, 370, 1045–1053 (1989)). However, experiments were not conducted to distinguish between the existence of a true intermediate $T_3R_3$ state or mixture composed of $T_6$ and $R_6$ forms (Wollmer et al., Biol. Chem. Hoppe-Seyler, 370, 1045–1053 (1989)).

DESCRIPTION OF PREFERRED EMBODIMENTS

Figure 1:
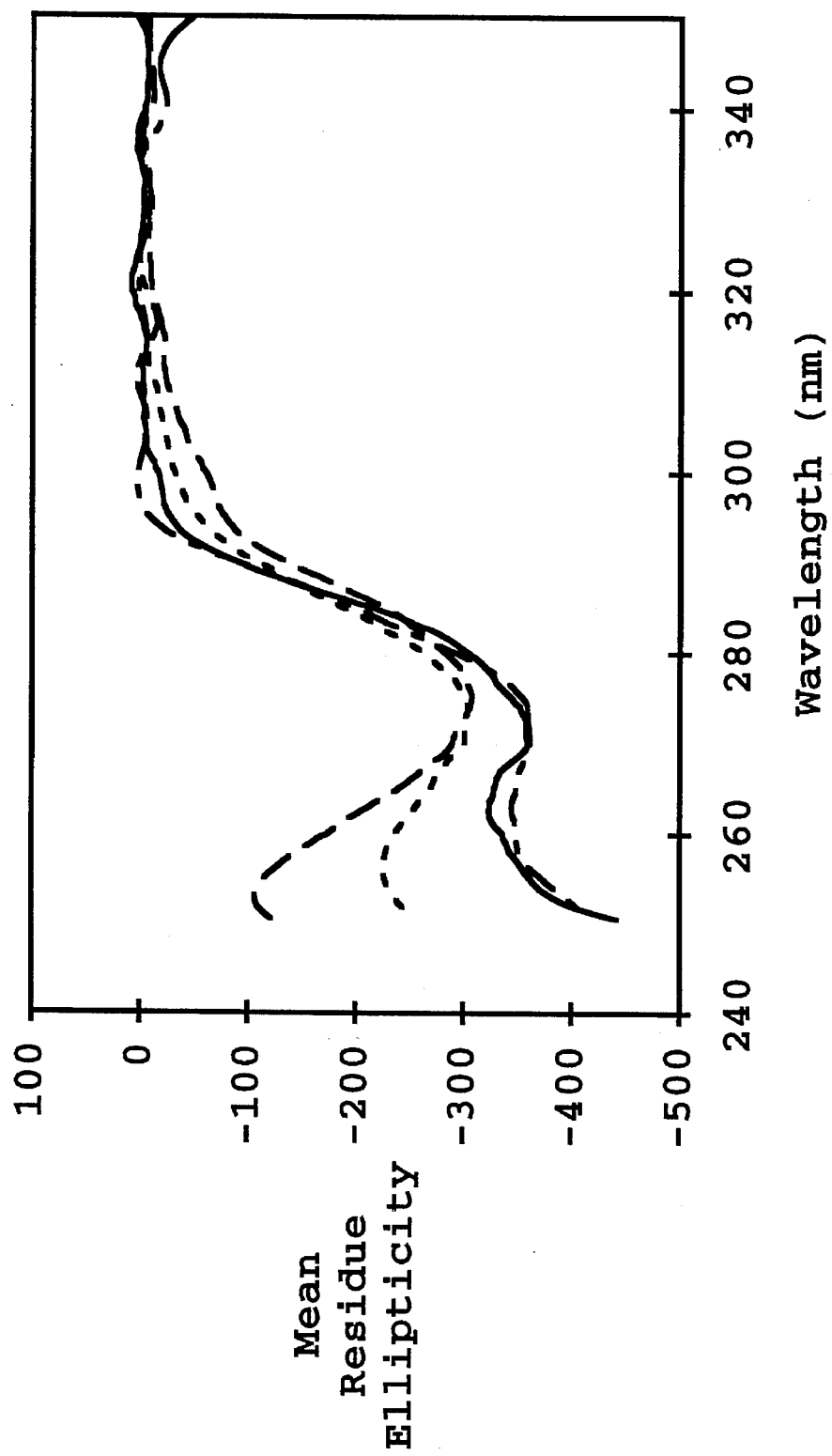
FIG. 1 is a graph showing near-UV circular dichroism spectra of biosynthetic human insulin (BHI) without m-cresol (---); $Asp^{B1}$ insulin without m-cresol (...); BHI with 0.1% m-cresol (__); $Asp^{B1}$ insulin with 0.1% m-cresol (-.-.). All samples contained 0.5 mol Zn per mol protein. The units of the ordinate are deg.cm2.dmol$^{-1}$.

The present invention relates to an insulin analog of the formula and selected from the group consisting of SEQ ID NO:1 as an A chain properly cross-linked to SEQ ID NO:2 as a B chain at the Cys at A and B chain positions 7 and a pharmaceutically acceptable salt of the analog.

Further, the present invention relates to a zinc ion hexamer insulin analog having a formula and selected from the group consisting of SEQ ID NO:1 as an A chain properly cross-linked to SEQ ID NO:2 as a B chain through the Cys A and B chain positions 7.

Further still, the present invention relates to a method of treating hyperglycemia which comprises administering to a patient in need thereof an effective amount of an insulin analog of the formula and selected from the group consisting of SEQ ID NO:1 as an A chain properly cross-linked to SEQ ID NO:2 as a B chain at the Cys A and B chains positions 7, and a pharmaceutically acceptable salt thereof.

Finally, the present invention relates to a pharmaceutical composition comprising, in a pharmaceutically acceptable diluent, an insulin analog of the formula and selected from the group consisting of SEQ ID NO:1 as an A chain properly cross-linked to SEQ ID NO:2 as a B chain at the Cys at A and B chains positions 7 and a pharmaceutically acceptable salt thereof.

In particular, Xaa at position 13 is Glu or preferably Gln.

For purposes of the present invention, as disclosed and claimed herein, the following terms and abbreviations are as defined below.

BHI- biosynthetic human insulin.

Cross-link—the formation of disulfide bonds between cysteine residues. A properly cross-linked native human insulin or insulin analog contains three disulfide bridges. The first disulfide bridge is found between the cysteine residues at positions 6 and 11 of the A-chain. The second bridge is between the cysteine 7 positions in the A and B chain. The third bridge is between position 20 in the A chain and position 19 in the B chain.

All amino acid abbreviations used in this disclosure are those accepted by the United States Patent and Trademark Office as set forth in 37 C.F.R. §1.822(b)(2) (1990).

In particular, the present invention relates to insulin analogs of the formula SEQ ID NO:1 which is Gly Ile Val Glu Gln Cys Cys Thr Ser Ile Cys Ser Leu Tyr
1              5                    10

Gln Leu Glu Asn Tyr Cys Asn
15              20 properly cross-linked to SEQ ID NO:2 which is

Asp Val Asn Gln His Leu Cys Gly Ser His Leu Val Xaa Ala
1              5                    10
Leu Tyr Leu Val Cys Gly Glu Arg Gly Phe Phe Tyr Thr Pro
15              20                   25
Lys Thr
    30 and a pharmaceutically acceptable salt thereof, wherein Xaa at position B of SEQ ID NO:2 (insulin B-chain) is Glu or Gln.

The insulin analogs of the present invention have an enhanced propensity to dimerize or otherwise self-associate to higher molecular weight forms, either in a solution which contains zinc or a solution which is zinc-free. Since the analogs are generally associated together in solution, a slow onset of activity is achieved upon administration.

As mentioned hereinabove, the invention includes pharmaceutically acceptable salts of the insulin analogs. Preferred such salts are alkali metal and alkaline earth metal salts, particularly sodium, potassium, magnesium, calcium, or combinations of these salts as well as transition metal salts such as zinc and cobalt.

The insulin analogs of this invention are prepared by any of a variety of recognized peptide synthesis techniques including classical (solution) methods, solid-phase methods, semisynthetic methods and the more recently available recombinant DNA methods.

In the solid-phase technique, the amino acid sequence is constructed sequentially from an initial, insoluble, resin-supported C-terminal amino acid. Techniques for the solid phase method are described by J. Stewart et al., Solid-Phase Peptide Synthesis, Freeman and Co., San Francisco, 1–103 (1969)).

In general, in the solid-phase method, the amino acid corresponding to the C-terminal amino acid residue of the desired peptide is anchored to an insoluble resin support, and the peptide chain then is formed beginning at the resin-supported C-terminal amino acid. Individual amino acids are introduced sequentially until the desired amino acid sequence is obtained. Alternatively, small peptide fragments can be prepared and introduced into the peptide chain in the desired order. The peptide chain remains attached to the resin throughout synthesis, and, upon completion of the chain the peptide is cleaved from the resin.

The peptide chain is attached to the polystyrene resin by means of an ester linkage formed between the carboxyl group of the C-terminal moiety and a specific methylene group present on the resin matrix as a site for such attachment.

The amino acids are coupled using techniques well known in the art for the formation of peptide bonds. One method involves converting the amino acid to a derivative that will render the carboxyl group more susceptible to reaction with the free N-terminal amino group of the peptide fragment. For example, the amino acid can be converted to a mixed anhydride by reaction of a protected amino acid with ethyl chloroformate, phenyl chloroformate, sec-butyl chloroformate, or isobutyl chloroformate. Alternatively, the amino acid can be converted to an active ester such as a 2,4,5-trichlorophenyl ester, a pentachlorophenyl ester, a p-nitrophenyl ester, a N-hydroxysuccinimide ester, or an ester formed from 1-hydroxybenzotriazole.

Another coupling method involves use of a suitable coupling agent, such as N,N'-dicyclohexylcarbodiimide (DCC) or N,N'-diisopropylcarbodiimide (DIC). Other appropriate coupling agents will be apparent to those skilled in the art. (See Schroder and Lubke, The Peptides, Academic Press, Chapter III (1965), which is incorporated herein by reference.

It should be recognized that the α-amino group of each amino acid employed in the peptide synthesis must be protected during the coupling reaction to prevent side reactions involving the reactive α-amino function. It should also be recognized that certain amino acids contain reactive side-chain functional groups (e.g., sulfhydryl, E-amino, β-and α-carboxyl, imidazole, guanido and hydroxyl), and that such functional groups must also be protected both during the initial and subsequent coupling steps. Suitable protecting groups are known in the art. See for example, Protective Groups in Organic Chemistry, M. McOmie, Editor, Plenum Press, N.Y., (1973) and U.S. Pat. No. 4,617,149, which are incorporated herein by reference.

In selecting a particular protecting group, certain conditions must be observed. An α-amino protecting group (1) must render the α-amino function inert under the conditions employed in the coupling reaction, (2) must be readily removable after the coupling reaction under conditions that will not remove side chain protecting groups and will not alter the structure of the peptide fragment, and (3) must eliminate the possibility of racemization upon activation immediately prior to coupling. A side chain protecting group (1) must render the side chain functional group inert under the conditions employed in the coupling reaction, (2) must be stable under the conditions employed in removing the α-amino protecting group, and (3) must be readily removable upon completion of the desired amino acid sequence under reaction conditions that will not alter the structure of the peptide chain.

It will be apparent to those skilled in the art that the protecting groups known to be useful for peptide synthesis will vary in reactivity to the agents employed for their removal. For example, certain protecting groups, such as triphenyl methyl and 2-(p-biphenyl)isopropyloxycarbonyl are very labile and can be cleaved under mild acid conditions. Other protecting groups, such as t-butyloxycarbonyl, t-amyloxycarbonyl, adamantyloxycarbonyl, and p-methoxybenzyloxycarbonyl, are less labile and require moderately strong acids, such as trifluoroacetic, hydrochloric, or boron trifluoride in acetic acid, for their removal. Still other protecting groups, such as benzyloxycarbonyl, halobenzyloxycarbonyl, p-nitrobenzyloxycarbonyl, cycloalkyloxycarbonyl, and isopropyloxycarbonyl, are even less labile and require stronger acids, such as hydrogen fluoride, hydrogen bromide, or boron trifluoroacetate in trifluoroacetic acid, for their removal.

Upon completion of the desired peptide sequence, the protected peptide must be cleaved from the resin support, and all protecting groups must be removed. The cleavage reaction and removal of the protecting groups may be accomplished simultaneously or stepwise. When the resin support is a chloromethylated polystyrene resin, the bond anchoring the peptide to the resin is an ester linkage formed between the free carboxyl group of the C-terminal moiety and one of the many chloromethyl groups present on the resin matrix. It will be recognized that the anchoring bond can be cleaved by reagents which are known to be capable of breaking an ester linkage and of penetrating the resin matrix. One especially convenient method is by treatment with liquid anhydrous hydrogen fluoride. This reagent not only will cleave the peptide from the resin but will also remove all protecting groups. Hence, use of this reagent will directly afford the fully deprotected peptide. When it is desired to cleave the peptide without removing protecting groups, the protected peptide-resin can undergo methanolysis to give the protected peptide in which the C-terminal carboxyl group is methylated. The methyl ester can then be hydrolyzed under mild, alkaline conditions to give the free C-terminal carboxyl. The protecting groups on the peptide chain then can be removed by treatment with a strong acid, such as liquid hydrogen fluoride. A particularly useful technique for methanolysis is that in which the protected peptide-resin is treated with methanol and potassium cyanide in the presence of crown ether.

Another method for cleaving the protected peptide from the resin is by ammonolysis or by treatment with hydrazine.

If desired, the resulting C-terminal amide or hydrazide can be hydrolyzed to the free C-terminal carboxyl, and the protecting groups can be removed conventionally.

It will also be recognized that the protecting group present on the N-terminal α-amino group may be removed preferentially either before or simultaneous with the cleavage of the protected peptide from the resin support.

The A and B chains of the insulin analogs of the present invention can also be prepared via recombinant DNA methodology. In their preparation, a nucleotide sequence coding for the desired peptide of the A or B chain is prepared using now-routine techniques for such synthesis. These methods generally involve preparation of oligonucleotides coding both for fragments of the desired coding sequence and for the complementary sequence thereof. The oligonucleotides are designed to provide overlap of one fragment of the coding sequence with two fragments of the complementary sequence and vice versa. The oligonucleotides are paired and joined, ultimately producing the desired gene sequence.

The sequence is inserted into a cloning vector at a location which permits the peptide product for which it codes to be expressed. The construction of plasmids capable of expressing proinsulin and proinsulin analogs is described in Chance et al., European Patent Publication No. 0 383 472, published Aug. 22, 1990, the entire teaching of which is herein incorporated by reference.

The A and B chains of the insulin analogs of the present invention may also be prepared via a proinsulin-like precursor molecule using recombinant DNA techniques. See Frank et al., Peptides: Synthesis-Structure-Function, Proc. Seventh Am. Pept. Symp., Eds. D. Rich and E. Gross, 729 to 738 (1981) which is incorporated herein by reference.

The step of combining the individual A and B chains, however produced, may be achieved by the method of Chance et al., Peptides: Synthesis, Structure and Function: Proc. of Seventh American Peptide Symposium 721–728 (1981) which is incorporated herein by reference.

In the present invention $Phe^{B1}$ of human insulin was replaced by aspartic acid, resulting in the stable formation of an allosteric Zn-hexamer intermediate conformation ($T_3R_3$) that is otherwise only induced by ligands. In the $Asp^{B1}$ insulin $T_3R_3$ conformation, one trimer is in the T state while the other trimer is in the R state which requires the movement of over 30 Å of the N-termini of the B chains. For one of the trimers the $Asp^{B1}$ side chain of the insulin analog permanently substitutes or compensates for the interactions normally provided by the extrinsic ligand. Addition of phenolic ligand to $Asp^{B1}$ insulin induces the other trimer to the R state. The allosteric conformational states were determined by circular dichroism spectroscopy of $Asp^{B1}$ insulin compared to the standard allosteric states of insulin. The formation of a constitutive R-state of the insulin hexamer provides further insight into insulin allostery.

The present invention is also particularly based on the surprising result that change of the $phe^{B1}$ to asp combined with $glu^{B13}$ to $gln^{B13}$ results in an insulin analog that self-associates to an R-state conformation in the absence of any extrinsic ligands. The $asp^{B1}$ side chain of this mutated insulin permanently substitutes or compensates for the interactions normally provided by the phenolic-type extrinsic ligands. The $gln^{B13}$ substitution induces this analog insulin to self-associate in the absence of Zn ligand. This constitutive property of $asp^{B1}$ $gln^{B13}$-insulin results in a ~70% delay in the time action profile compared to Humulin R (a short acting synthetic human insulin, Eli Lilly, Indianapolis, Ind.). Since the dissociation of insulin hexamer is dependent on the local concentrations of extrinsic ligands, the protracted time-action of this analog can have decreased propensity to dissociate to monomer at the subcutaneous injection site. This analog is soluble in currently used HUMULIN R diluent, thus avoiding the inherent complications of suspension formulations of the currently available slow-acting insulins.

In the present specification the abbreviations are UV, ultra-violet; CD, circular dichroism; HPLC, high-performance liquid chromatography; T & R-states, apoinsulin and ligand-bound insulin hexamers respectively; BHI, biosynthetic human insulin. Tris, 2-amino-2-(hydroxymethyl)-1,3-propanediol. The conventional nomenclature is used for the A and B chain amino acids.

The following Example 1 shows the preparation of $Asp^{B1}$ insulin. Example 2 shows the preparation and testing of $Asp^{B1}Gln^{B13}$.

The following examples are provided as a means of illustrating the present invention and are not to be construed as a limitation thereon.

Example 1

Experimental Procedures

Materials

Zinc-free biosynthetic human insulin (BHI) was obtained from Eli Lilly & Co., Indianapolis, Ind. Tert-BOC (tertiary butyloxycarbonyl) amino acids used in the synthesis of the $Asp^{B1}$ insulin analog were purchased from Applied Biosystems, Inc., Foster City, Calif. Potassium thiocyanate was obtained from CEM Science, and m-cresol was purchased from Aldrich Chemical Co., Inc., Milwaukee, Wis. All other chemicals were of analytical grade or higher.

Methods

Protein stock solutions were prepared by dissolving a known mass of protein in either 20 mM Tris or 50 mM sodium phosphate and 50 mM sodium chloride, pH 7.8, followed by zinc oxide addition to a final concentration of 0.5 mol Zn per mol of protein monomer. The pH of the solution was readjusted to pH 7.8 as needed. The protein stock concentrations were determined by UV absorbance using an AVIV model 14DS double-beam spectrophotometer. Protein concentrations were calculated based on extinction coefficients of 1.05 $(mg/ml)^{-1}.cm^{-1}$ for BHI at 276 nm (Frank et al., Diabetes, 21 (Suppl. 2) 486–491 (1972)) and 1.06 $(mg/ml)^{-1}.cm^{-1}$ for $Asp^{B1}$ insulin at 276 nm. All circular dichroism measurements were obtained using an AVIV Model 62DS spectrometer (Lakewood, N.J.) with results reported as mean residue ellipticity (MRE) having units of $deg.cm^2.dmol^{-1}$.

Methods

An applied Biosystems model 430A synthesizer was used to synthesize the B chain sequence of human insulin with an aspartic acid substitution at the $B^1$ site, replacing the natural phenylalanine($Phe^{B1}$). This modified B chain was purified by reversed-phase HPLC and characterized by amino acid analysis. The purified B chain was then coupled to purified human insulin A chain by the method of chain combination. The resultant chain coupling product was purified by reversed-phase HPLC and size-exclusion chromatography. The $Asp^{B1}$ insulin was characterized by mass spectrometry and amino acid analysis.

Analog Purification

The $Asp^{B1}$ was purified by reversed-phase HPLC resulting in a final purity of >95% according to analytical reversed-phase HPLC. Subsequent mass spectral data demonstrated a mass of 5,774.7 which agrees with the theoretical value of 5,775.4. Results of amino acid analysis indicate the presence of an additional fourth aspartic acid residue and the absence of one of the three native phenylalanines which is consistent with the $Asp^{B1}$ insulin.

m-Cresol and KSCN Titrations

Samples were prepared by combining a constant volume of protein stock, either BHI or $Asp^{B1}$ insulin, with various ratios of m-cresol stock solutions and 20 mM Tris pH 7.8 to obtain the desired m-cresol concentrations. To mix the samples, the protein stock was added last, followed by gentle swirling of the solution to a final protein concentration of ~2mg/ml.

Samples of KSCN titrations were prepared in a similar manner, combining a constant volume of protein stock with various ratios of KSCN and 20 mM Tris stocks at pH 7.8 to obtain the desired KSCN concentration. The protein fraction was added last and mixed by gentle swirling of the sample to a final protein concentration of ~2 mg/ml.

All samples were measured by far-UV CD at 23° C. using a 0.01 cm CD cell. The signal at 224 nm was recorded as a function of either m-cresol or KSCN concentration.

Circular Dichroism Smectroscopy

Near- and far-UV CD spectra were collected at various points along the m-cresol and KSCN titration curves for both BHI and $Asp^{B1}$ insulin. To further explore secondary structure, the far-UV CD spectra were collected from 250 nm to 200 nm using a 0.01 cm cuvette. To gain insight into the environment of the aromatic and disulfide amino acids the near-UV CD spectra were collected from 350 to 250 nm using a 0.1 cm cell.

Equilibrium Ultracentrifugation

Samples were prepared by dissolving a protein stock of $Asp^{B1}$ insulin in 20 mM Tris pH 7.8, to approximately 3 mg/ml in the presence of 0.5 mol Zn per mol protein monomer. Equilibrium ultracentrifugation data was collected at 22° C. at equally spaced radial intervals using a Beckman Model XLA analytical ultracentrifuge Fullterton, Calif. Standard 30 mm and 12 mm centerpieces along with custom-made 3 mm centerpieces all made from charcoal-filled epon were used. Raw data from the chart recorder was converted to concentration versus radius using the internal calibration factors of the scanner. The weight average molecular weight was calculated according to the equation:

$$MW = RT/(1-Vp)\omega^2 \cdot 1r \cdot 1/C \cdot dC/dr$$

where R is the gas constant, T is the temperature, ω is the rotor speed, r is the radius, C is the concentration, ρ is the solvent density, and assuming ideal solutions. $Asp^{B1}$ insulin was assumed to have the same partial specific volume as insulin, 0.73 ml/g. Least squares smoothing methods were used to calculate C and dC/dr.

Spectroscopic Characterizations of $ASp^{B1}$ insulin Allosterism

To gain insight into changes in the environment of cystine and aromatic residues, BHI and $Asp^{B1}$ insulin solutions containing 0.5 mol Zn per mol protein monomer were monitored in the near-UV in the presence and absence of m-cresol. The near-UV CD spectra of BHI and $Asp^{B1}$ insulin with and without 0.1% m-cresol are shown in FIG. 1. Marked differences are apparent in the Zn-induced hexameric state of BHI and the $Asp^{B1}$ insulin analog. Three distinct types of spectra are shown, representing the characteristic hexameric conformations $T_6$, $T_3R_3$, and $R_6$. The near-UV spectrum of the Zn-BHI hexamer without phenolics or inorganic ions is representative of the $T_6$ state and is in excellent agreement with past studies (Renscheidt et al., Eur. J. Biochem., 142, 7–14 (1984); Wollmer et al., Biol. Chem. Hopper-Seyler, 368, 903–911 (1987)). The structural change that BHI undergoes in the presence of 0.1% m-cresol is shown by the increase in ellipticity at 255 nm. This increased ellipticity is representative of previous findings (Renscheidt et al., Eur. J. Biochem., 142, 7–14 (1984); Wollmer et al., Biol. Chem. Hoppe-Seyler, 368, 903–911 (1987)) and corresponds to the ligand-induced conformational change to the $R_6$ state. The most striking observation is the near-UV CD spectra of $Asp^{B1}$ insulin. In the absence of helix-inducing m-cresol, $Asp^{B1}$ insulin's spectrum is markedly different than that of BHI under identical conditions. An increase in ellipticity is observed near 255 nm, with a signal intermediate between BHI's "native" $T_6$ state and BHI's final m-cresol induced $R_6$ state. This intermediate conformation initially occupied by $D^{B1}$ insulin is a self-induced $T_3R_3$ like state, a conformation normally only initiated by the addition of limited amounts of phenolic compounds or inorganic anions (Brader & Dunn, TIBS, 16 341–345 (1991)). With the addition of 0.1% m-cresol, the self-induced $T_3R_3$ state of $Asp^{B1}$ insulin is converted to the $R_6$ state, identical in the near-UV CD to that of BHI under identical conditions. Therefore, BHI and $Asp^{B1}$ insulin attain the same final conformational state in the presence of 0.1% m-cresol.

Figure 2:
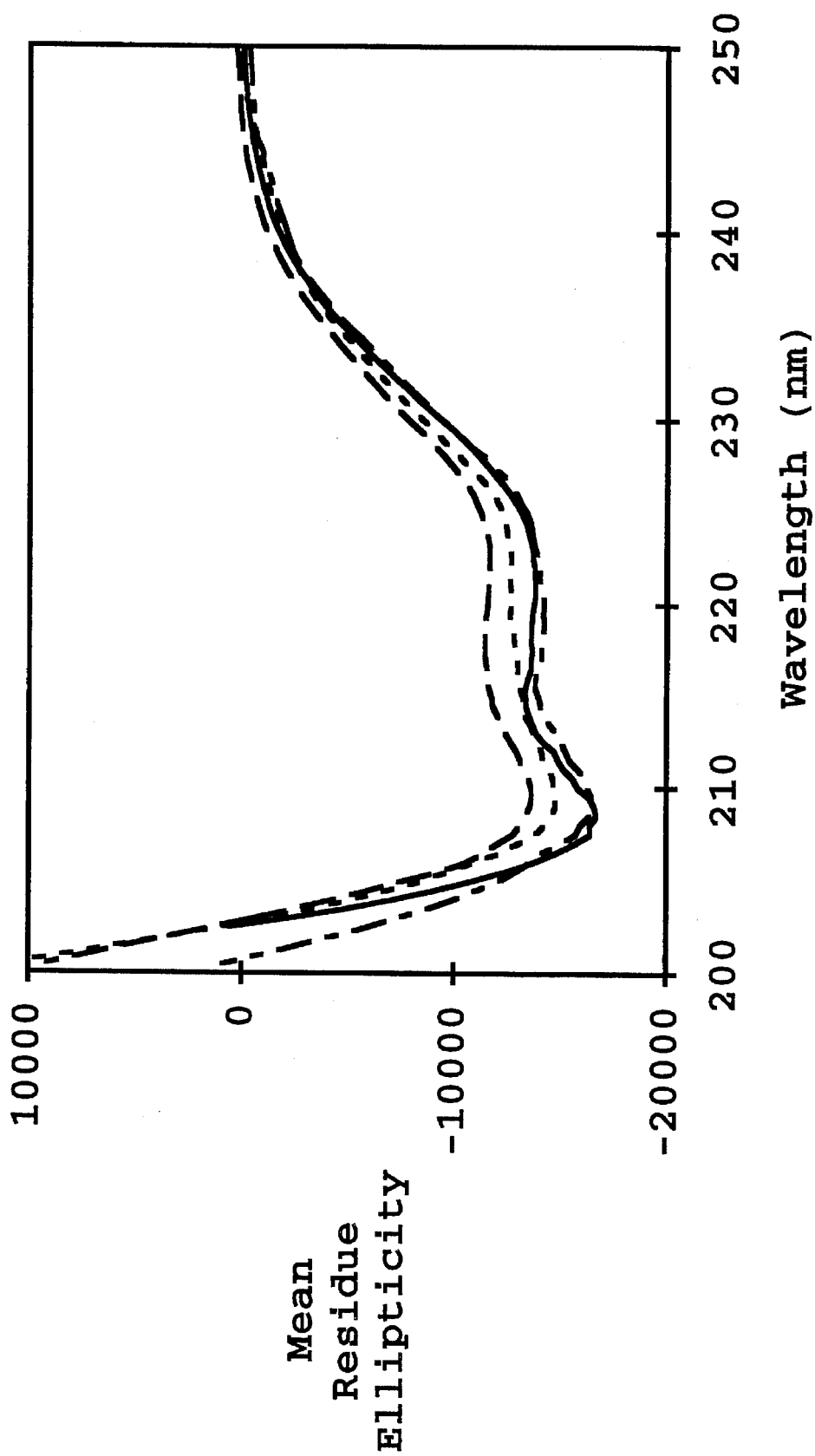
FIG. 2 is a graph showing far-UV circular dichroism spectra of BHI without m-cresol (---); $Asp^{B1}$ insulin without m-cresol (..); BHI with 0.1% m-cresol (__); $ASP^{B1}$ insulin with 0.1% m-cresol (-.-.). All samples contained 0.5 mol Zn per mol protein. The units of the ordinate are deg.cm2.dmol$^{-1}$.

The conclusions obtained from the near-UV CD were corroborated by the far-UV CD spectra in FIG. 2. The far-UV CD spectra are particularly sensitive to changes in protein secondary structure, and the results in FIG. 2 clearly differentiate the $T_6$, $T_3R_3$, and $R_6$ like forms. As seen by the ellipticities at 209 nm and 224 nm, $Asp^{B1}$ insulin in the absence of m-cresol possesses greater helical content than does BHI under the same conditions. This supports the position that $Asp^{B1}$ insulin hexamer conformation, in the absence of allosteric affecters, is not the same as that of BHI. In 0.1% m-cresol, both BHI and $Asp^{B1}$ insulin show an increase in helix, resulting in identical final $R_6$ states. Therefore, the spectra of phenolic-free $Asp^{B1}$ insulin is intermediate between the BHI $T_6$ and $R_6$ state and indicative of a constitutive $T^3R_3$ like state.

Ligand Induced Conformational Changes (m-Cresol and KSCN Titrations)

Phenolic compounds are known to cooperatively bind to hexameric insulin and induce a complete transition from a T state to an R state (Brader & Dunn, TIBS, 16, 341–345 (1991)). However, inorganic ions such as $SCN^-$ only induce a change from the $T_6$ state to a stable intermediate $T^3R_3$ conformation; one trimer is not convertible to the R state by inorganic ions (Kruger et al., Biol. Chem. Hoppe-Seyler, 371, 669–673 (1990)).

Figure 3:
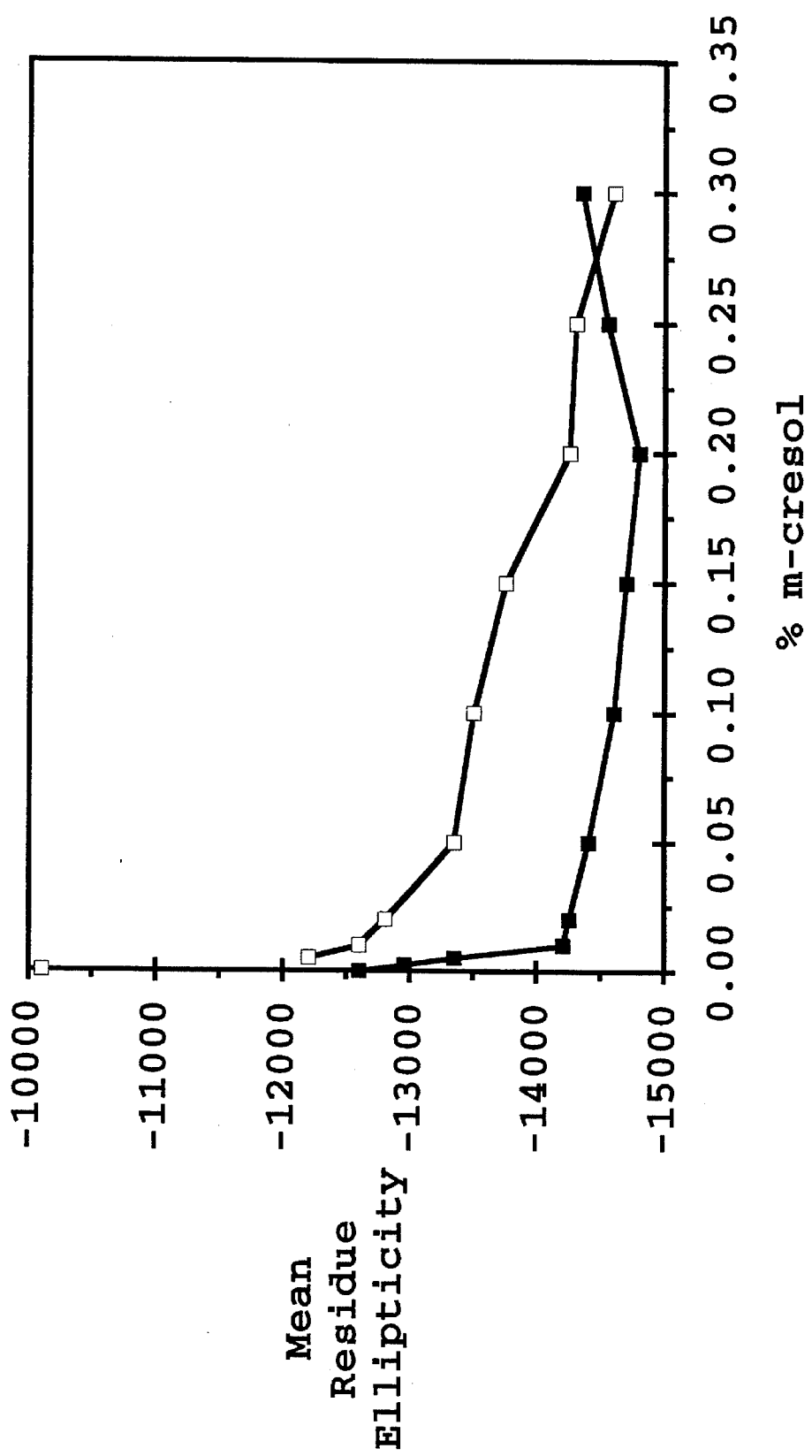
FIG. 3 is a graph of a m-cresol titration of BHI and $Asp^{B1}$ insulin using far-UV circular dichroism. Shown are the m-cresol induced $T_6$->$R_6$ transition for BHI □ and the $T_3R_3$->$R_6$ transition for $Asp^{B1}$ insulin ■. All samples contained 0.5 mol Zn per mol protein. The units of the ordinate are deg.cm$^2$.dmol$^{-1}$.

The m-cresol titration curves for BHI and $Asp^{B1}$ insulin are shown in FIG. 3. Two important points can be elucidated from these results, both of which support the spectroscopic data represented in FIGS. 1 and 2. First, in comparing the total ellipticity change between initial and final points on the titration curve, the change seen for $Asp^{B1}$ is one-half that seen for BHI. The initial mean residue ellipticity (MRE) for Asp$^{B1}$ insulin also occurs at the intermediate point of BHI's full titration curve, indicating that one trimer is already in the R state. Second, the end points of titration are of the same MRE value, indicating the same final conformation of $R_6$ is attained.

Figure 4:
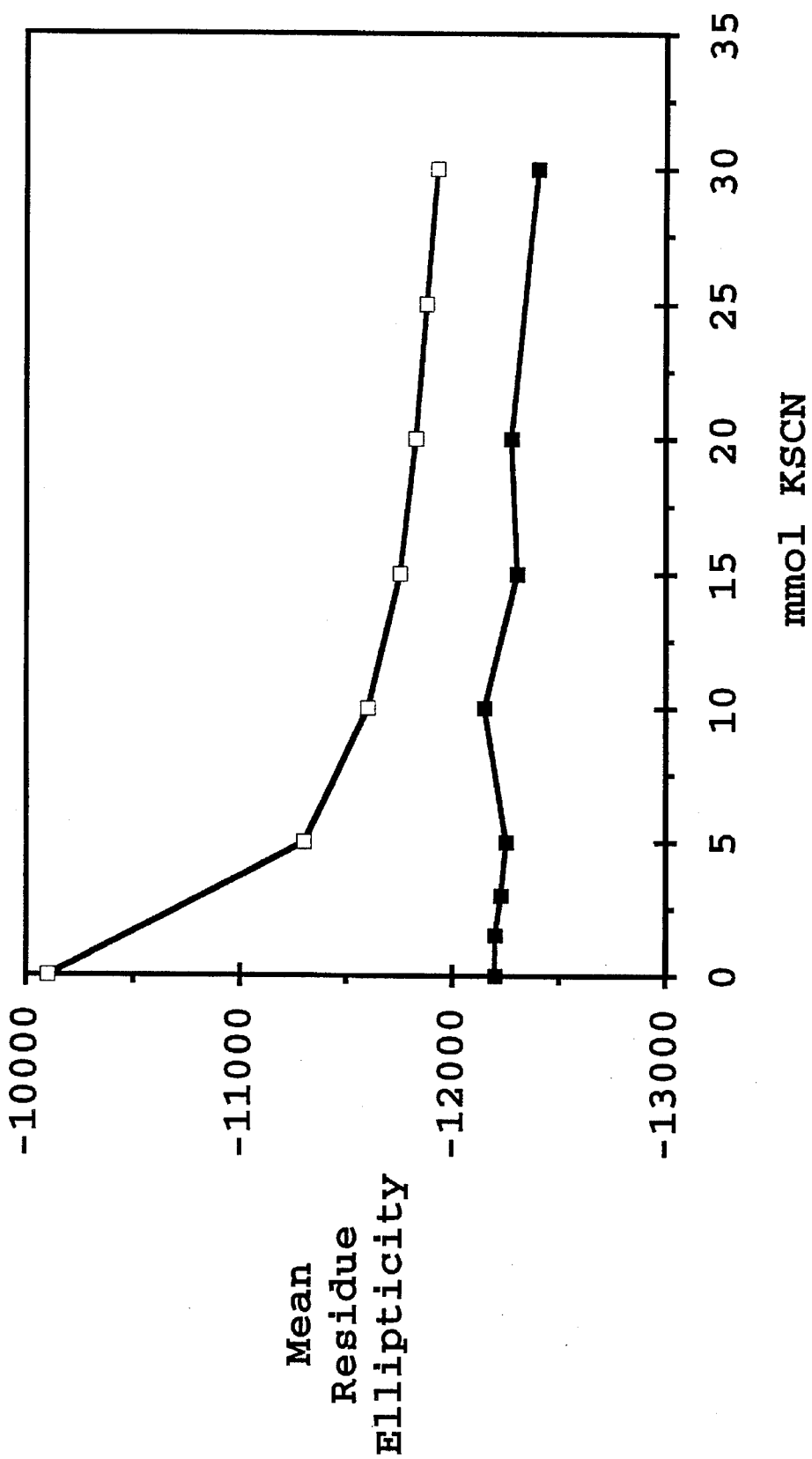
FIG. 4 is a graph showing KSCN titration of BHI and $Asp^{B1}$ insulin using far-UV circular dichroism. Shown are the KSCN induced $T_6$->$T_3R_3$ transition for BHI □ and the absence of any transition beyond the initial $T_3R_3$ state for $Asp^{B1}$ insulin ■. All samples contained 0.5 mol Zn per mol protein. The units of the ordinate are deg.cm2.dmol$^{-1}$.

The KSCN titration curves for BHI and Asp$^{B1}$ insulin are shown in FIG. 4. Comparing the KSCN titration curve in FIG. 4 with the m-cresol titration curve in FIG. 3, shows that BHI undergoes only one-half of the transformation from T –>R in the presence of KSCN. In accordance with past findings (Kruger et al, Biol. Chem. Hoppe-Seyler, 371 669–673 (1990)), KSCN induces the R state in only one trimer, thus locking BHI in the $T_3R_3$ state. In Asp$^{B1}$ insulin, however, the absence of any transition upon addition of KSCN indicates that the insulin analog is already in the $T_3R_3$ state and is unaffected by anion addition.

Aggregation State Analysis

The T–>R transition has only been observed in the hexamer state, making the aggregation state analysis of critical importance. Equilibrium ultracentrifugation of Zn-Asp$^{B1}$ insulin, containing 0.5 mol of Zn per mol of protein in 20 mM Tris buffer pH 7.8, demonstrated a weight average molecular weight of a hexamer over a protein concentration of 1.5 to 5 mg/ml. Thus, the aggregation states of Zn-Asp$^{B1}$ insulin and Zn-BHI (Grant et al., Biochem. J., 126 433–440 (1972)) are identical.

Insulin and ASP$^{B1}$ Insulin Allostery

Minor changes in a protein's primary structure can often result in dramatic changes in chemical and physical properties. Such a dramatic alteration is present for Asp$^{B1}$ insulin. By the single amino acid replacement of aspartic acid for phenylalanine at the $B^1$ site, a stable allosteric hexamer intermediate, $T_3R_3$, is formed in the presence of Zn. This intermediate state is otherwise only induced by allosteric ligands. FIG. 1 shows that according to the near-UV CD spectrum, Asp$^{B1}$ insulin is intermediate between the T and R states of insulin. Kruger et al. (Kruger et al., Biol. Chem. Hoppe-Seyler, 371 669–673 (1990)) has interpreted the changes in the near-UV CD that accompany the T–>R transition as changes in the ellipticity of disulfide bonds. This interpretation is consistent with the X-ray structure of Zn-phenol insulin hexamer which reveals a phenol hydrophobic binding pocket composed of A chain residues from one dimer and the $B^1$–$B^8$ helical segment from the adjacent dimer (Derewenda et al., Nature, 338 594–596 (1989)). In the rhombohedral crystals a hydrogen bond occurs between phenol and the carbonyl oxygen of $C^{A6}$ (Smith & Dodson, Biopolymers, 32 441–445 (1992)). In the monoclinic crystals the bound phenol donates a hydrogen bond to $C^{A6}$ carbonyl oxygen and accepts a hydrogen bond from the $C^{A11}$ amide nitrogen (Derewenda et al., Nature, 338 594–596 (1989)). Thus, binding of phenols could directly alter the ellipticity of the $A^6$–$A^{11}$ and/or the $A^7$–$B^7$ disulfide bonds that are in close proximity to the phenol binding site. The far-UV CD spectrum of ASP$^{B1}$ insulin (FIG. 2) confirms an intermediate structure between the T–>R transitions. FIGS. 3 and 4 show that ASP$^{B1}$ insulin is convertible to an $R_6$ structure with cresol but KSCN is unable to induce a change. These results are interpreted to indicate that Zn-Asp$^{B1}$ insulin without added allosteric ligands is a stable $T_3R_3$ like intermediate, and the trimer which is normally converted by small anionic ligands such as SCN-is specifically in a R like state. The other trimer of Zn-Asp$^{B1}$ insulin is capable of undergoing a conversion to the R state by the addition of m-cresol (FIG. 3). According to equilibrium ultracentrifugation, Zn-Asp$^{B1}$ insulin is a hexamer under the conditions utilized in this study.

Explanation for the Self-induced Allosterism of Asp$^{B1}$ Insulin

Two possible mechanisms are proposed for the self-induced allosterism of Asp$^{B1}$ insulin. The first mechanism involves a helix-stabilizing interaction between the negative charge of the β-carboxy of Asp$^{B1}$ and the positive charge of the α-helix dipole at the N-terminus of the B chain. In the R state, the helix is extended to the N-terminus and includes residues $B^1$–$B^{19}$. The four backbone amides of the N-terminal residues of α-helices are not hydrogen bonded and create a positive dipole (Hol et al., Nature, 273, 443–446 (1978); Shoemaker et al., Nature, 326 563–567 (1987)). Amino acids with negatively charged side chains are preferred at the N-terminal ends of helices and have been shown to help stabilize helices through charge-dipole interactions (Shoemaker et al., Nature, 326 563–567 (1987); Presta & Rose, Science, 240, 1632–1641 (1988); Richardson & Richardson, Science, 240, 1648–1652 (1988); Serrano, et al., Nature 342, 296–299 (1989)). Therefore, Asp$^{B1}$ would be expected to stabilize the R state through a charge-dipole interaction. In this mechanism it is not clear why only one trimer is transformed to the R state. Perhaps the stabilizing energy provided by the charge-dipole interaction is sufficient to convert one trimer but not sufficient to convert the other trimer due to the negative cooperativity that exists between the trimers (Kruger et al., Biol. Chem. Hoppe-Seyler, 371, 669–673 (1990)). According to this mechanism, the results of FIGS. 3 and 4 would indicate that the trimer that is transformed by small anionic ligands is the trimer that is converted to the R state by the charge-dipole interaction. A further extension of this mechanism is that small anionic salts are capable of converting one of the trimers of insulin to the R state through a salt-shielding effect of the helix dipole that would otherwise have unfavorable interaction with the positive charge of the α-amino N-terminus of the B chain.

A second proposed mechanism for the self-induced allosterism of Asp$^{B1}$ is that the B-carboxyl of Asp$^{B1}$ provides a coordination site for one of the two Zn ions. A recent X-ray structure of a rhombohedral $R_6$ insulin/phenol complex identified a seventh phenol binding site in which a phenol is located within coordination distance (zinc-oxygen distance of 2.1 Å) of one of the Zn ions (Smith & Dodson, Biopolymers, 32, 441–445 (1992)). For the rhombohedral $R_6$ hexamer the two trimers are distinct with one trimer containing the Zn atom tetrahedrally coordinated to three $H^{B10}$ atoms and one Cl and the other trimer containing the Zn atom tetrahedrally coordinated to three $H^{B10}$ atoms and one phenolate (Smith & Dodson, Biopolymers, 32, 441–445 (1992)). In this mechanism the Asp$^{B1}$ moiety is substituting for the Zn liganded phenolate. Since only one trimer of the rhombohedral $R_6$ hexamer has the coordinated phenolate, this mechanism nicely explains the resultant $T_3R_3$ nature of Asp$^{B1}$ insulin hexamer. The X-ray structure of the rhombohedral $R_6$ insulin/phenol complex shows that Phe$^{B1}$ is in near proximity to the seventh phenol binding site (Smith & Dodson, Biopolymers, 32, 441–445 (1992)). The exact position of Phe$^{B1}$ cannot be determined from the crystal structure since Phe$^{B1}$ is not evident from the electron density maps presumably due to high thermal motion or disorder (Smith & Dodson, Biopolymers, 32, 441–445 (1992)).

The results show that $Asp^{B1}$ insulin exists as a stable $T_3R_3$ intermediate in the absence of inducible allosteric ligands. Such dramatic changes in the conformational properties of allosteric proteins are achievable by the single amine acid alteration. These results emphasize the delicate balance between conformers of allosteric proteins.

The allosteric nature of insulin plays a significant role in the pharmaceutical use of insulin. Most pharmaceutical formulations of insulin likely contain high populations of the R state which have important consequences to stability (Brange et al. Pharm. Res., 9, 715–726 (1992a); Brange et al., Pharm. Res., 9, 727–734 (1992b) Brange & Langkjaer, Acta Pharm. Nord., 4, 149–158 (1992)) and perhaps to the time action profile. Other in vive biological consequences of the T–>R transition have not been demonstrated. A stable $T_3R_3$ intermediate that is self-induced and does not require extrinsic ligands for allosteric transformation is extremely useful for determining the biological differences of the T and R states.

Example 2

Preparation of $AsP^{B1}$, $Gln^{B13}$ Human Insulin B-Chain

An Applied Biosystems, Inc. (Foster City, Calif.) 430A peptide synthesizer (including software revision 1.4) was used to prepare a crude peptidyl resin. 0.5 Millimoles (mMol) of the starting solid phase resin (t-BOC-Thr (Bzl) $OCH_2$ PAM resin Applied Biosystems, Inc., Foster City, Calif.) was used (0.72 mMol/g ×0.77 g, 10% excess). All amine acids used were BOC (BOC is tertiary butyloxycarbonyl) protected and, except for glutamic acid and aspartic acid, all were used directly as received (i.e., in cartridges from Applied Biosystems, Inc.; each cartridge contained approximately 2 mMol of protected amine acid). Glutamic acid and aspartic acid were obtained from commercial sources and transferred to cartridges such that each cartridge contained approximately 2 mMol of the desired protected amine acid. The crude peptidyl resin was dried under vacuum at room temperature for 4 hours and its weight compared to the starting weight to assure reasonable weight gain. A small portion of sample was submitted for amino acid analysis to ensure that the desired amino acids were added in the correct proportion.

The peptide was cleaved from the peptidyl resin and side-chain deprotected by stirring for approximately 1 hour at 0° C. in a solution of 10 parts (v/w) HP (containing 5% v/v p-thiocresol and 5% v/v m-cresol) to 1 part peptidyl resin. After removal of most of the HF by vacuum, the peptide was precipitated in chilled ethyl ether. After several rinses with chilled ethyl ether followed by vacuum filtration, the peptide was dissolved in approximately 200 ml of 7M guanidine-HCl, pH 10, containing 0.1M tris, 35 mg/ml $Na_2SO_3$ and 25 mg/ml $Na_2S_4O_6$. The solution was adjusted to pH 8.8 with 5N NaOH and allowed to stir vigorously for 1.7 hours at room temperature.

The resulting S-sulfonated peptide solution was loaded onto a 5×215 cm column of Sephadex G-25 (coarse) at room temperature. The sample was eluted at 70 ml/min at room temperature using 50 mM $NH_4HCO_3$ in 10% acetonitrile. The effluent was monitored at 276 nm and a pool of the desired effluent was made, frozen and lyophilized.

Combination of $Asp^{(B1)}$, $Gln^{(B13)}$ Human Insulin B-Chain with Human Insulin A-Chain The combination of the A- and B-chains was accomplished by the procedure of Chance et al. using recombinantly produced A-chain as described in EPO 0 383,472 supra. 6.13 g of the recombinant DNA-derived A-Chain S-sulfonate and 1.38 g of the synthetic $Asp(B^1)$, $Gln(B^{13})$ B-chain S-sulfonate were combined in a beaker and dissolved in 662 ml 0.1M glycine at 4° C. The pH of the solution was adjusted to 10.5 with 5N NaOH, and kept at 4° C. A dithiothreitol (DTT) solution at 15.5 mg/ml was prepared in 0.1M glycine buffer at ambient temperature, adjusted to pH 10.5 with 5N NaOH and then cooled at 4° C.

48.7 ml of the DTT solution were quickly added to the solution for combined A-chain and B-chain S-sulfonates $(SH/SSO^{-3}=1.1)$. The reaction solution was pH adjusted to 10.5 and stirred at 4° C. in a 2L beaker for 29.5 hours. Acetic acid was added to quench the reaction, dropping the pH to 5.5.

The resulting precipitated sample was centrifuged at 2000 rpm at 4° C. for 20 minutes. The supernate was decanted and the pellets held at 4° C. (see below). 140-ml portions of chilled acetone were added to 70-ml portions of the supernate to precipitate additional product. Centrifugation at 4° C., 2000 rpm was used to separate the insoluble material. The supernate was discarded and the pellets combined with the original pellets (above). The pellets were dissolved in a volume of 375 ml of 7M guanidine HCl, 10 mM $Na_2S_4O_6$ containing 10% acetonitrile, pH 7. The sample was solvent exchanged by loading at 70 ml/min onto a 5×200 cm G-25 (coarse) and eluting at room temperature, 70 ml/min using a pH 7 buffer containing 0.1M $(NH_4)_2HPO_4$, 0.001M $Na_2S_4O_6$ in 10% acetonitrile. A 1540 ml pool was collected. The pool was purified using a 2.2×25 cm DuPont (Rockland Technologies) ZORBAX C-8 reversed-phase HPLC column, eluting with a linear (increasing) gradient of acetonitrile in 0.1M pH 7 $(NH_4)_2HPO_4$, 0.001M $Na_2S_4O_6$ at room temperature. After assaying by analytical HPLC selected fractions were pooled, diluted 2× and purified over a VYDAC C-18 (The Munhall Co., Worthington, OH) column, using 0.1% TFA (Applied Biosystems, Inc., Foster City, Calif.) and a linear (increasing) gradient of acetonitrile at room temperature. Selected fractions monitored by analytical HPLC were pooled and lyophilized. Additional purification was done by dissolving the lyophilized sample in a solution of 20 mM pH 7 Tris, 0.001M $Na_2S_4O_6$ in 30% acetonitrile. This solution was loaded onto a 1×10 cm Pharmacia (Piscataway, N.J.) MONO-Q column at 4 ml/min, and eluted with 20 mM pH 7 TRIS, 0.001M $Na_2S_4O_6$ in 30% acetonitrile and a linear (increasing) gradient of NaCl at room temperature. Following analytical HPLC analyses of selected fractions a pool was made, diluted 4× with MILLI-Q water (Millipore, Inc., Bedford, Mass.) and loaded onto a 1×25 cm Vydac C-18 column (The Munhall Co., Worthington, Ohio) for final desalting/purification using 0.1% TFA and acetonitrile (as above). Final analytical HPLC of selected fractions, followed by pooling and lyophilization resulted in 10.7 mg of material with greater than 98% purity.

The structure was verified by Fast Atom Bombardment Mass Spectrometry (FAB/MS) and by amino acid analysis. Results of the FAB/MS gave a molecular weight of 5774.8 (Theory: 5774.5 ). The amino acid composition was as follows based on aspartic acid as molar unity (theoretical amino acid ratios in parentheses): Asp, 4.00 (4); Thr, 2.77 (3); Ser, 2.42 (3); Glu, 6.91 (7); Gly, 3.84 (4); Ala, .86 (1);

½ Cys, 4.06 (6); Val, 3.36 (4); Ile, 1.67 (2); Leu, 5.62 (6); Tyr, 3.57 (4); Phe, 2.00 (2); His, 2.14 (2); Arg, 0.95 (1).

The results of testing for circular dichroism and helicity of $Asp^{B1}Gln^{B13}$ are shown in Tables 1 and 2.

TABLE 1

Circular Dichroism[1]

| Sample | Wavelength | | |
|---|---|---|---|
| | 276 nm | 251 nm | 224 nm |
| Human Insulin | −226 | −101 | −9983 |
| Zn + Human Insulin | −305 | −121 | −10892 |
| Zn + m-cresol + Human Insulin | −335 | −425 | −13488 |
| $asp^{B1}gln^{B13}$ Insulin | −307 | −109 | −12481 |
| Zn + $asp^{B1}gln^{B13}$ Insulin | −291 | −426 | −14555 |
| Zn + m-cresol + $asp^{B1}gln^{B13}$ Insulin | −384 | −431 | −14092 |

[1]Multiple measurements show a variation of 3%.

TABLE 2

α-Helical Analysis

| Sample | % Helix Measured[1] | % Helix Theoretical |
|---|---|---|
| Human Insulin | 47 | 47[2] |
| Zn + Human Insulin | 48 | 47 |
| Zn + m-cresol + Human Insulin | 66 | 63[3] |
| $asp^{B1}gln^{B13}$ Insulin | 56 | |
| Zn + $asp^{B1}gln^{B13}$ Insulin | 65 | |
| Zn + m-cresol + $asp^{B1}gln^{B13}$ Insulin | 64 | |

[1]Determined by CONTIN analysis from the circular dichroism spectra.
[2]According to NMR analysis (Kline, A. D., Justice, R. M., Jr., Biochemistry, 29, 2906–2913 (1990)) which shows identical helical content as determined by x-ray crystallography of Zn-Human Insulin.
[3]Corresponding to the report of Derewenda, U., Derewenda, Z., Dodson, E. J., Dodson, G. G., Reynolds, C. D., Smith, G. D., Sparks, C., and Swenson, D., Nature, 338, 594–596 (1989)).

Example 3

The following sets of experiments were performed to aid in the evaluation of $Asp^{B1}Gln^{B13}$ human insulin as an intermediate-acting insulin. The time-action profiles of $Asp^{B1}Gln^{B13}$ human insulin, HUMULIN L (an intermediate-acting insulin formulation) and HUMULIN R, (Eli Lilly, Indianapolis, Ind.) (a short acting insulin formulation) were determined in two sets of depancreatized dogs, and the results were compared.

Experiments were carried out in conscious, adult (1–2 years of age) male and female beagles (Marshall Farms, North Rose, N.Y.) weighing 9.5–14.7 kg. At least three weeks prior to the day of study, a laparotomy was performed under isoflurane (Anaquest, Madison, Wis.) anesthesia (Brevital used for induction of anesthesia; Eli Lilly & Co., Indianapolis, Ind.) during which the entire pancreas was excised (Markowitz, J., et al., Experimental Surgery Including Surgical Physiology, pp. 236–252 (1964)). Upon closure of the abdominal cavity, a cut-down was made in the left inguinal region, and a Silastic (Dow Corning Corp., Midland, Mich.) catheter was inserted in the femoral artery. The free end of the catheter was passed subcutaneously to the back using a trocar needle. The catheter was then filled with a glycerol/heparin solution (3:1, v/v; final heparin concentration of 250 KIU/ml; glycerol from Sigma Chemical Co., St. Louis, Mo., and sodium heparin from Elkins-Sinn Inc., Cherry Hill, N.J.), and the free end was knotted and placed in a subcutaneous pocket to allow complete closure of the skin. Penicillin G (600,000 U, i.m.; The Butler Co., Columbus, Ohio) and Demerol (Sterling Animal Health Products, New York, N.Y.) were administered postoperatively.

The diabetic animals were maintained on a twice daily feeding/insulin administration regimen (Hill's Science Diet, Canine Maintenance, Hill's Pet Products, Inc., Topeka, Kans.; Porcine NPH insulin, Eli Lilly & Co., Indianapolis, Ind.), with VIOKASE (A. H. Robins Co., Richmond, Va.) added to the food to replace pancreatic enzymes. Food administration was adjusted to maintain a constant body weight, and insulin doses were adjusted to minimize glycosuria.

Blood was drawn just prior to the study day to determine the health of the animal. Only animals with hematocrits above 38% and leukocyte counts below $16,000/mm^3$ were used.

The day before the experiment, NPH insulin was withheld from the test animal. Food (plus VIOKASE) was administered as usual. Four units of regular porcine insulin (Eli Lilly & Co., Indianapolis, Ind.) were administered with the large afternoon meal to aid in the disposition of the nutrient load. The afternoon before the experiment, the free end of the arterial catheter was exteriorized from the subcutaneous pocket through a small incision made under local anesthesia (2% Lidocaine, The Butler Co., Columbus, Ohio), and the dog was fitted with the tether system jacket and collar assembly.

The morning of the experiment, the contents of the catheter were aspirated, the catheter was flushed with saline, and an extension line (protected by a stainless steel tether) was attached to the catheter. The dog was placed in a metabolic cage, and the catheter extension line and tether were attached to a swivel system to allow the dog to move freely about the cage. Fifteen minutes after entering the cage and approximately seventeen hours after the last feeding, the first control sample was taken. A second control sample was taken fifteen minutes later, and the test substance (0.3 U/kg; a U-100 formulation of HUMULIN L, HUMULIN R or $Asp^{B1}Gln^{B13}$ human insulin, the latter assumed to be equipotent to native human insulin on a molar basis; was injected subcutaneously in the dorsal aspect of the neck. $Asp^{B1}Gln^{B13}$ human insulin was formulated identically to Humulin R and contained 3.5 mg/ml of protein, 2.5 mg/ml m-cresol, 16 mg/ml glycerol and 0.02 mg/ml zn. Over the next six to fifteen hours, blood samples were taken at five to thirty minute intervals and collected in vacuum blood collection tubes containing sodium heparin (Terumo Medical Corp., Elkton, Md.). After removing the plasma, the cells were washed three times with normal saline, resuspended in saline, and infused back into the animal. At the conclusion of the experiment, the animal was anesthetized (isoflurane), the catheter was flushed with fresh saline and filled with the glycerol/heparin mixture, the free end of the catheter was knotted and placed subcutaneously as described earlier, and the dog was treated with antibiotics as before.

Plasma glucose levels were determined the day of the study using a coupled hexokinase procedure in a clinical chemistry analyzer (Kornberg, A., et al., Methods in Enzymology 1:323–328 (1955); Bathelmai, W., et al., Klin. Wochenschr. 40:585 (1962)) (Monarch, Instrumentation Laboratory, Lexington, Mass.).

HUMULIN R was evaluated in a set of five dogs; HUMULIN L and $Asp^{B1}Gln^{B13}$ human insulin were evaluated in a second set of three dogs to allow partial pairing of the database. The results are shown in Tables 3 and 4.

TABLE 3

Change of glucose from basal conc. (mg/dl) in the depancreatized dog

| Time | Humulin R[1] | SEM[3] | asp$^{B1}$gln$^{B13}$ insulin[2] | SEM[3] |
|---|---|---|---|---|
| 0 | 1 | 5 | 5 | 4 |
| 15 | −1 | 5 | −5 | 4 |
| 20 | 5 | 6 | | |
| 25 | −12 | 6 | | |
| 30 | −25 | 5 | −27 | 5 |
| 35 | −43 | 9 | | |
| 40 | −64 | 5 | | |
| 45 | −90 | 6 | −55 | 7 |
| 50 | −115 | 16 | | |
| 55 | −134 | 16 | | |
| 60 | −158 | 19 | −98 | 20 |
| 65 | −184 | 21 | | |
| 70 | −198 | 23 | | |
| 75 | −216 | 24 | −129 | 27 |
| 80 | −232 | 27 | | |
| 85 | −252 | 32 | | |
| 90 | −266 | 34 | −172 | 28 |
| 95 | −283 | 36 | | |
| 100 | −302 | 38 | | |
| 105 | −318 | 37 | −190 | 25 |
| 115 | −345 | 37 | | |
| 120 | | | −234 | 20 |
| 125 | −363 | 38 | | |
| 135 | −381 | 35 | −256 | 17 |
| 150 | −399 | 30 | −289 | 16 |
| 165 | −414 | 28 | −314 | 13 |
| 180 | −420 | 24 | −335 | 12 |
| 195 | −423 | 21 | −350 | 13 |
| 210 | −423 | 21 | −371 | 9 |
| 225 | −417 | 19 | −381 | 10 |
| 240 | −405 | 16 | −391 | 11 |
| 255 | −394 | 18 | −394 | 13 |
| 270 | −379 | 21 | −410 | 14 |
| 285 | −364 | 25 | −415 | 14 |
| 300 | −352 | 27 | −421 | 18 |
| 315 | −332 | 31 | −419 | 19 |
| 330 | −304 | 39 | −424 | 22 |
| 345 | −286 | 43 | −421 | 24 |
| 360 | −266 | 47 | −423 | 28 |
| 375 | −241 | 49 | −419 | 28 |
| 390 | | | −416 | 32 |
| 405 | | | −413 | 35 |
| 420 | | | −395 | 48 |
| 435 | | | −374 | 55 |
| 450 | | | −356 | 63 |
| 465 | | | −346 | 71 |
| 480 | | | −334 | 78 |
| 495 | | | −297 | 87 |

[1]average from five dogs
[2]average from three dogs (separate dogs from the Humulin R study)
[3]the standard error of the mean

TABLE 4

Humulin L data

| Humulin L (0.3 U/kg, SC) | Average |
|---|---|
| 0 | 6 |
| 15 | −6 |
| 45 | −59 |
| 75 | −149 |
| 105 | −227 |
| 135 | −290 |
| 165 | −340 |
| 195 | −378 |
| 225 | −410 |
| 255 | −450 |
| 285 | −470 |
| 315 | −491 |
| 345 | −504 |
| 375 | −516 |
| 405 | −524 |
| 435 | −522 |
| 465 | −523 |
| 495 | −510 |
| 525 | −511 |
| 555 | −490 |
| 585 | −474 |
| 615 | −458 |
| 645 | −441 |
| 675 | −426 |
| 705 | −412 |
| 735 | −386 |
| 765 | −372 |
| 795 | −353 |
| 825 | −343 |
| 855 | −310 |
| 885 | −292 |
| 915 | −260 |

As is well known to those skilled in the art, the data in dogs is directly translatable to humans. This is shown for instance in Goeders, L. A., Esposito, L. A., and Peterson, M. E., Domestic Animal Endocrinology 4, 43–50 1987). Table 3 particularly shows that Asp$^{B1}$Gln$^{B13}$ insulin has a self induced conformation in absence of ligands which enables it to be long acting. This result was unexpected.

As noted previously, in the absence of metal ions for phenolic ligands the insulin analogs of the present invention have an increased propensity to self-associate to higher molecular weight forms. Thus, upon administration of one or more of said analogs, a slow onset of activity is achieved. The insulin analogs of the present invention are effective in treating hyperglycemia by administering to a patient in need thereof an effective amount of an insulin analog. As used herein the term "effective amount" refers to that amount of one or more insulin analogs of the present invention needed to lower or maintain blood sugar levels either therapeutically or prophylactically. This amount typically may range from about 5 units up to about 200 units or more per day (or about 0.175 to about 7 mg assuming approximately 28.6 units per mg). The dosages are equivalent to those for human insulin. However, it is to be understood that the amount of the insulin analog(s) actually administered will be determined by a physician in light of the relevant circumstances including the condition being treated (i.e., the cause of the hyperglycemia) the particular analog to be administered, the chosen parenteral route of administration, the age, weight and response of the individual patient and the severity of the patient's symptoms. Therefore, the above dosage ranges are not intended to limit the scope of the invention in any manner.

The insulin analogs of the invention are administered to a patient in need thereof (i.e., a patient suffering from hyperglycemia) by means of pharmaceutical compositions containing an effective amount of at least one insulin analog containing an aspartic acid residue at position 1 of the B chain in combination with one or more pharmaceutically acceptable excipients or carriers. For these purposes, the pharmaceutical compositions may typically be formulated so as to contain about 100 units per ml or similar concentrations containing an effective amount of the insulin analog(s). These compositions are typically, though not necessarily, parenteral in nature and may be prepared by any of a variety of techniques using conventional excipients or carriers for parenteral products which are well known in the art. See, for example, Remington's Pharmaceutical Sciences, 17th Edition, Mack Publishing Company, Easton, Pa., USA (1985) which is incorporated herein by reference. For example, dosage forms for parenteral administration may be prepared by suspending or dissolving the desired amount of at least one of the insulin analogs in a non-toxic liquid vehicle suitable for injection such as an aqueous medium and sterilizing the suspension or solution. An accompanying vial or vehicle can be provided for purposes of mixing prior to administration. Pharmaceutical compositions adapted for parenteral administration employ diluents, excipients and carriers such as water and water-miscible organic solvents such as glycerin, sesame oil, groundnut oil, aqueous propylene glycol, N,N'-dimethylformamide and the like. Examples of such pharmaceutical compositions include sterile, isotonic, aqueous saline solutions of the insulin analogs which can be buffered with a pharmaceutically acceptable buffer and which are pyrogen free. Additionally, the parenteral pharmaceutical formulation may contain preservatives such as phenol or meta-cresol. Agents to adjust pH of the final product such as sodium hydroxide or hydrochloric acid may also be used.

The insulin analogs of the present invention may also be formulated into pharmaceutical compositions suitable for intranasal administration. Such compositions are disclosed in detail in European Patent Application 0200383 A3 which is incorporated herein by reference. Briefly, such compositions are formulated with one or more pharmaceutically acceptable diluents, a pharmaceutically acceptable amount of an alkali metal salt, the ammonium salt, or the free acid of a substantially zinc-free insulin, and optionally, an absorption enhancing amount of at least one absorption enhancing agent selected from the group consisting of (1) oleic acid or an ester or salt thereof, (2) a liquid form sorbitan fatty acid ester, (3) a liquid form polyoxyethylene derivative of a sorbitan fatty acid ester, and (4) a liquid form hydroxypolyoxyethylene-polyoxypropylene-polyoxyethylene copolymer.

It is intended that the foregoing description be only illustrative of the present invention and that the present invention be limited only by the hereinafter appended claims.

---

We claim:
1. An insulin analog monomer having the formula

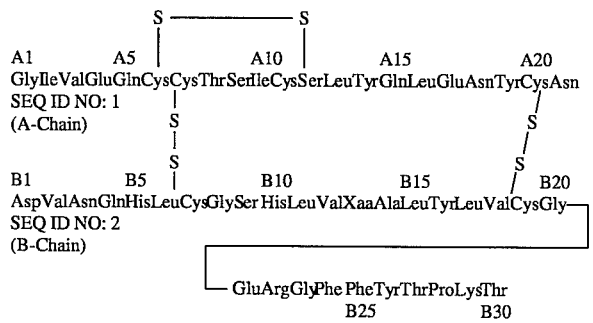

wherein Xaa at amino acid position B13 is selected from the group consisting of Glu and Gln.

2. The insulin analog monomer of claim 1, wherein Xaa at amino acid position B13 is Gln.

3. The insulin analog monomer of claim 1, wherein Xaa at amino acid position B13 is Glu.

4. An insulin analog hexamer comprising six insulin analog monomers, each monomer having the formula of claim 1, wherein approximately zero to approximately two zinc ions are associated per hexamer.

5. The insulin analog hexamer of claim 4, wherein Xaa at amino acid position B13 of each insulin analog monomer is Gln, and wherein approximately zero zinc ions are associated per hexamer.

6. The insulin analog hexamer of claim 4, wherein Xaa at amino acid position B13 of each insulin analog monomer is Glu, and wherein approximately two zinc ions are associated per hexamer.

7. A pharmaceutical formulation comprising, in a pharmaceutically acceptable diluent, the insulin analog hexamer of claim 4.

8. The pharmaceutical formulation of claim 7, wherein Xaa at amino acid position B13 of each insulin analog monomer is Gln, and wherein approximately two zinc ions are associated per hexamer.

9. The pharmaceutical formulation of claim 7, wherein Xaa at amino acid position B13 of each insulin analog monomer is Glu, and wherein approximately two zinc ions are associated per hexamer.

10. A method of treating hyperglycemia which comprises administering to a patient in need thereof an effective amount of the insulin analog hexamer of claim 4.

11. The method of treating hyperglycemia of claim 10, wherein Xaa at amino acid position B13 of each insulin analog monomer is Gln, and wherein approximately zero zinc ions are associated per hexamer.

12. The method of treating hyperglycemia of claim 10, wherein Xaa at amino acid position B13 of each insulin analog monomer is Glu, and wherein approximately two zinc ions are associated per hexamer.

13. A pharmaceutical formulation comprising, in a pharmaceutically acceptable diluent, an insulin analog monomer having the formula

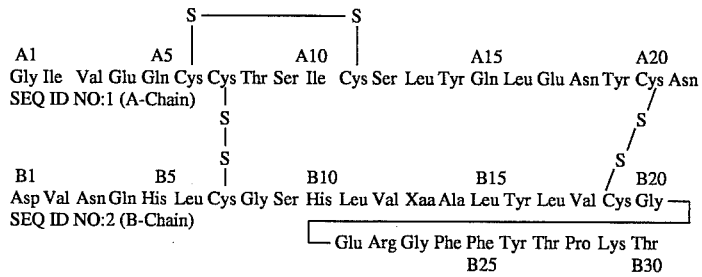

wherein Xaa at amino acid position B13 is selected from the group consisting of Glu and Gln.

14. The pharmaceutical formulation of claim 13, wherein Xaa at amino acid position B13 of the insulin analog monomer is Gln.

15. The pharmaceutical formulation of claim 13, wherein Xaa at amino acid position B13 of the insulin analog monomer is Glu.

16. A method of treating hyperglycemia which comprises administering to a patient in need thereof an effective amount of an insulin analog monomer having the formula

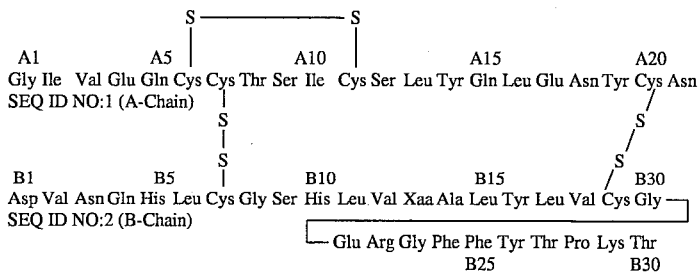
wherein Xaa at amino acid position B13 is selected from the group consisting of Glu and Gln.
17. The method of treating hyperglycemia of claim 16 wherein Xaa at amino acid position B13 of the insulin analog monomer is Gln.
18. The method of treating hyperglycemia of claim 16 wherein Xaa at amino acid position B13 of the insulin analog monomer is Glu.
* * * * *

UNITED STATES PATENT AND TRADEMARK OFFICE
CERTIFICATE OF CORRECTION

PATENT NO. : 5,559,094

DATED : September 24, 1996

INVENTOR(S) : Brems David N. et al

It is certified that error appears in the above-indentified patent and that said Letters Patent is hereby corrected as shown below:

Column 1, line 44 reads "Q-helix...." should read -- α-helix.--.

Column 3, line 24 reads "substituting gluB13..." should read --substituting should read glnB13--.

Column 3, line 31 reads "injection of a acidic..." should read --injection of a neutral--.

Column 3, line 51 reads "deg.cm2.dmol$^{-1}$." should read -- deg.cm$^2$.dmol$^{-1}$--.

Column 3, line 56 reads "deg.cm2.dmol$^{-1}$." should read -- deg.cm$^2$.dmol$^{-1}$--.

Column 4, line 3 reads "deg.cm2.dmol$^{-1}$." should read -- deg.cm$^2$.dmol$^{-1}$--.

Column 8, line 55 reads "Methods" should read --Synthesis and Isolation of Asp$^{B1}$ Insulin--.

Column 9, line 62 reads "of ASP$^{B1}$ insulin..." should read --of Asp$^{B1}$ insulin--.

Column 10, line 58 reads "intermediate T$^3$R$_3$..." should read --intermediate T$_3$R$_3$--.

UNITED STATES PATENT AND TRADEMARK OFFICE
CERTIFICATE OF CORRECTION

PATENT NO. : 5,559,094                                                     Page 2 of 3

DATED : September 24, 1996

INVENTOR(S) : Brems David N. et al

It is certified that error appears in the above-indentified patent and that said Letters Patent is hereby corrected as shown below:

should read:

```
                      S ——————— S
                      |         |
   A1         A5      |  A10    |    A15              A20
   Gly Ile Val Glu Gln Cys Cys Thr Ser Ile Cys Ser Leu Tyr Gln Leu Glu Asn Tyr Cys Asn
   SEQ ID NO:1 (A-Chain)  |                                                    /
                          S                                                   S
                          |                                                  /
                          S                                                 S
   B1         B5          |  B10          B15              / B20
   Asp Val Asn Gln His Leu Cys Gly Ser His Leu Val Xaa Ala Leu Tyr Leu Val Cys Gly ┐
   SEQ ID NO:2 (B-Chain)        └─ Glu Arg Gly Phe Phe Tyr Thr Pro Lys Thr
                                                        B25            B30
```

UNITED STATES PATENT AND TRADEMARK OFFICE
CERTIFICATE OF CORRECTION

PATENT NO. : 5,559,094

DATED : September 24, 1996

INVENTOR(S) : BREMS David N.; BAKAYSA Diane L.

It is certified that error appears in the above-indentified patent and that said Letters Patent is hereby corrected as shown below:

Column 21, claim 8, line 57 reads "wherein approximately two zinc ions..." should read --wherein approximately zero zinc ions--.

Column 21, claim 1, lines 2-18 reads:

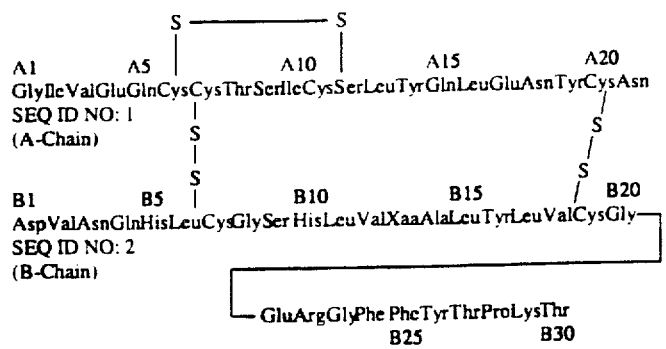

Signed and Sealed this

Third Day of June, 1997

BRUCE LEHMAN

Attest:

Attesting Officer

Commissioner of Patents and Trademarks